(12) United States Patent
Kuo et al.

(10) Patent No.: US 9,346,844 B2
(45) Date of Patent: May 24, 2016

(54) PROCESS FOR THE PRODUCTION OF FONDAPARINUX SODIUM

(71) Applicant: Scinopharm Taiwan, LTD., Shan-Hua, Tainan (TW)

(72) Inventors: Lung-Huang Kuo, Tainan (TW); Shang-Hong Chen, Chiayi (TW); Li-Ting Wang, Tainan (TW); Wen-Li Shih, Nantou (TW); Yuan-Xiu Liao, Tainan (TW)

(73) Assignee: SCINOPHARM TAIWAN, LTD., Tainan (TW)

( * ) Notice: Subject to any disclaimer, the term of this patent is extended or adjusted under 35 U.S.C. 154(b) by 166 days.

(21) Appl. No.: 13/950,716

(22) Filed: Jul. 25, 2013

(65) Prior Publication Data

US 2015/0031865 A1    Jan. 29, 2015

(51) Int. Cl.
*C07H 1/00* (2006.01)
*C07H 5/04* (2006.01)
*C07H 15/04* (2006.01)
*C07H 15/203* (2006.01)

(52) U.S. Cl.
CPC .................. *C07H 15/04* (2013.01); *C07H 1/00* (2013.01); *C07H 5/04* (2013.01); *C07H 15/203* (2013.01)

(58) Field of Classification Search
None
See application file for complete search history.

(56) References Cited

U.S. PATENT DOCUMENTS

| | | | |
|---|---|---|---|
| 4,818,816 | A | 4/1989 | Petitou et al. |
| 7,541,445 | B2 | 6/2009 | Seifert et al. |
| 8,288,515 | B2 | 10/2012 | Nadji et al. |
| 2005/0020536 | A1 | 1/2005 | Branellec et al. |
| 2009/0187013 | A1 | 7/2009 | Seifert et al. |
| 2011/0105418 | A1 | 5/2011 | Nadji et al. |
| 2011/0306757 | A1 | 12/2011 | Lopez-Belmonte Encina et al. |
| 2012/0116066 | A1 | 5/2012 | Patel et al. |
| 2012/0208993 | A1 | 8/2012 | Seifert et al. |
| 2013/0005954 | A1 | 1/2013 | Kovi et al. |
| 2015/0031866 | A1 | 1/2015 | Kuo |

FOREIGN PATENT DOCUMENTS

CN   103122012 A    5/2013

OTHER PUBLICATIONS

Weisstein, Eric W. "Ratio." From MathWorld—A Wolfram Web Resource. http://mathworld.wolfram.com/Ratio.html; viewed Aug. 18, 2015.*
PCT Application No. PCT/IB2013/002161, International Search Report and Written Opinion, Apr. 23, 2014, 10 pages.
PCT Application No. PCT/IB2013/002376, International Search Report and Written Opinion, Apr. 24, 2014, 7 pages.
Manikowski et al., "An Alternative Route for Fondaparinux Sodium Synthesis Via Selective Hydrogenations and Sulfation of Appropriate Pentasaccharides," Carbohydrate Research, Sep. 2012, vol. 361, pp. 155-161.
Codée, Jeroen D.C. et al., "A Modular Strategy Toward the Synthesis of Heparin-like Oligosaccharides Using Monomeric Building Blocks in a Sequential Glycosylation Strategy," *J. Am. Chem. Soc.* (2005) 127:3767-3773.
Ganguli, Anjali R. S. et al., "αβ Selectivity in the synthesis of 3-substituted, 4-methyl umbelliferone glycosides of N-acetyl glucosamine and chitobiose," *Assymetty* 16 (2005) 411-424.

* cited by examiner

*Primary Examiner* — Layla Berry
*Assistant Examiner* — Bahar Craigo
(74) *Attorney, Agent, or Firm* — Mintz, Levin, Cohn, Ferris, Glovsky and Popeo, P.C.

(57) ABSTRACT

The present invention provides novel processes for the preparation of Fondaparinux sodium by using the compound of formula ABC5

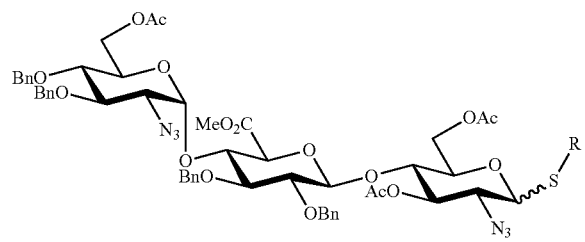

In some embodiments, the intermediates for the synthesis of Fondaparinux sodium, are also provided.

10 Claims, 2 Drawing Sheets

PROCESS FOR THE PRODUCTION OF FONDAPARINUX SODIUM

CROSS-REFERENCES TO RELATED APPLICATIONS

Not applicable

BACKGROUND OF THE INVENTION

Fondaparinux sodium (CAS 114870-03-0) is a member of oligosaccharides/heparins with a chemical name of O-[2-Deoxy-6-O-sulfo-2-(sulfoamino)-alpha-D-glucopyranosyl]-(1-4)-O-(beta-D-glucopyranurosonyl)-(1-4)-O-[2-deoxy-3,6-di-O-sulfo-2-(sulfoamino)-alpha-D-glucopyranosyl]-(1-4)-O-(2-O-sulfo-alpha-L-idopyranurosonyl)-(1-4)-O-[2-deoxy-1-O-methyl-6-O-sulfo-2-(sulfoamino)-alpha-D-glucopyranoside]decasodium salt, which developed by Choay, S. A. (see U.S. Pat. No. 4,818,816). The compound is a synthetic pentasaccharide Factor Xa inhibitor which is indicated as an anticoagulant drug used for the prevention of deep vein thrombosis in patients who have had orthopedic surgery as well as for the treatment of deep vein thrombosis and pulmonary embolism. It was approved by the United States Food and Drug Administration in 2001, marketed under the trade name Arixtra™ which is administrated subcutaneously.

The preparation process of Fondaparinux sodium disclosed in U.S. Pat. No. 4,818,816 is unsuitable for a large scale production since this process takes over 60 steps to afford a final product with low yield.

U.S. Pat. No. 8,288,515 applies protection and de-protection steps to prepare Fondaparinux sodium. However, the de-protection step results in low yields and consumes additional reaction time.

Another process is disclosed in U.S. 2011/0306757, but the additional reduction step of an azide needs further purification and the final N-sulfonation step remains in low yield (68%).

US 2012/0116066 describes the preparation of Fondaparinux sodium and its intermediates. However, the preparation of some intermediates such as EMod3 needs column purification. Moreover, the low α/β ratios in the coupling between C monomer and D monomer as well as numerous time-consuming procedures are not optimal.

In view of the above, there is still a need for a simple process with higher yield/purity for industrial preparation of Fondaparinux sodium.

BRIEF SUMMARY OF THE INVENTION

The present invention provides an economic process to prepare Fondaparinux sodium.

In one aspect, the present invention provides a novel process for the preparation of Fondaparinux sodium comprising reacting a compound of formula ABC5

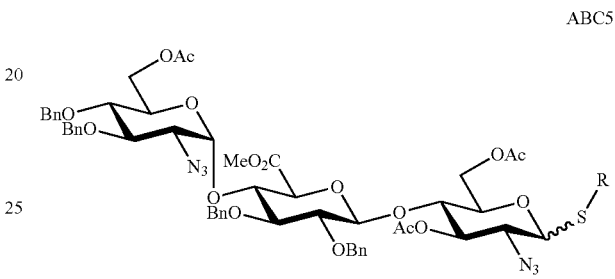

with a compound of formula DE4

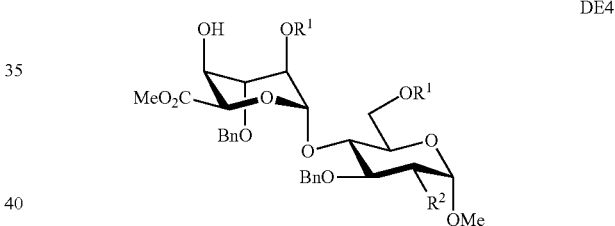

to obtain a compound of formula ABCDE1;

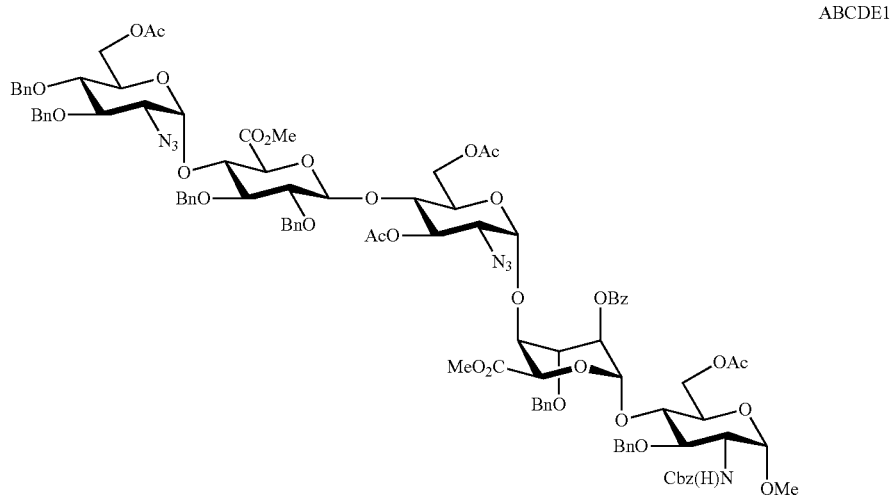

and then converting the compound of formula ABCDE1 to Fondaparinux sodium.

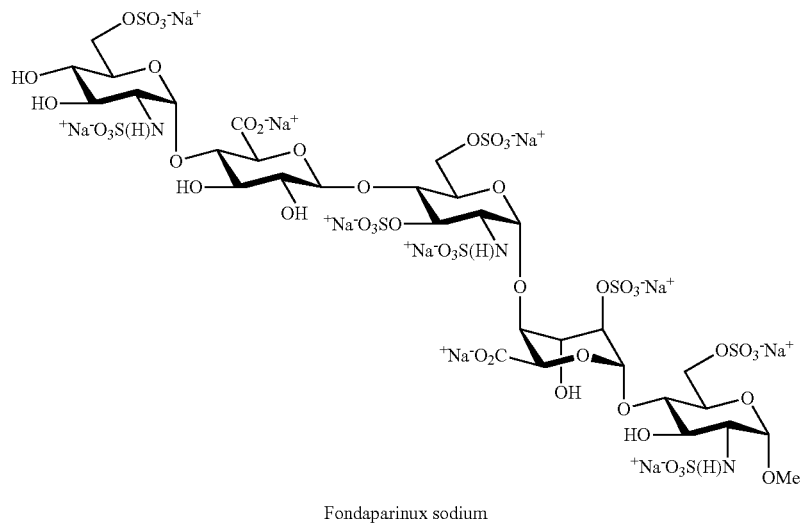

Fondaparinux sodium wherein R is selected from the group consisting of alkyl, phenyl, benzyl, substituted alkyl, substituted phenyl and substituted benzyl; $R^1$ is acetyl or benzyl; and $R^2$ is azide or NHCbz. The conversion of ABCDE1 to Fondiparinux sodium is described below in the detailed description of the invention.

In the methods described herein, ABCDE1 was initially prepared by reaction of donor trisaccharide ABC4

ABC4

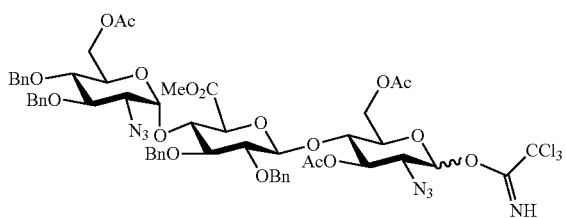

with acceptor disaccharide DE4,

DE4

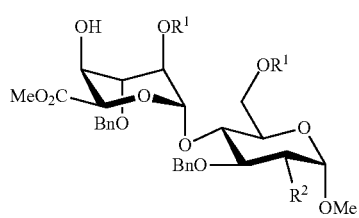

and obtained in 24% yield after being purified via column chromatography.

It was found that the trichloroacetimidate donor ABC4 reacts rapidly with water which causes a reduced yield. Although the thio-donor (ABC5) is less active, a rapid reaction with $H_2O$ can be avoided, which allows for a higher reaction yield. Surprisingly, the ABCDE1 obtained from ABC5, especially phenylsulfanyl intermediate ABC5a, shown below, was isolated without column chromatography and the yield increased to 65%.

ABC5a

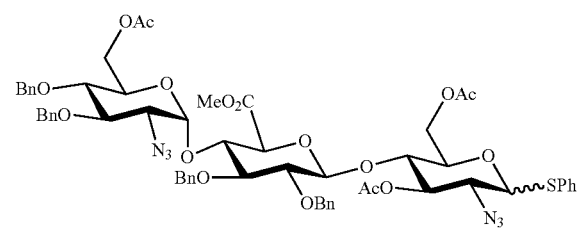

In a second aspect, the present invention provides a process for the preparation of a compound of formula ABC5 comprising converting a compound of formula ABC4

ABC4

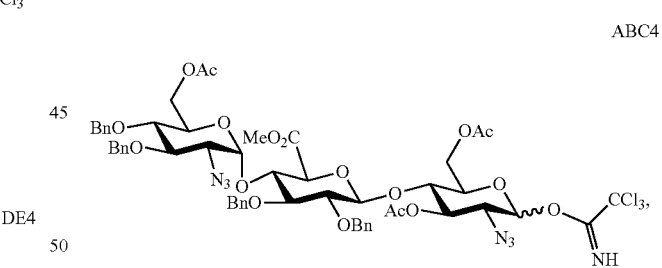

to the compound of formula ABC5

ABC5

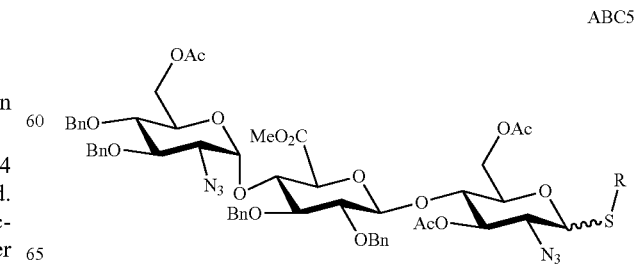

in the presence of a promoter; wherein R is selected from the group consisting of alkyl, phenyl, benzyl, substituted alkyl, substituted phenyl and substituted benzyl.

The promoter is selected from the group consisting of trialkylsilyls, trifluoromethanesulfonates, and mixtures of trialkylsilyls and trifluoromethanesulfonates. In some embodiments, the promoter is selected from the group consisting of tert-butyldimethylsilyl trifluoromethanesulfonate (TBSOTf), timethylsilyl trifluoromethanesulfonate (TMSOTf), triethylsilyl trifluoromethanesulfonate (TESOTf) and mixtures thereof.

In a third aspect, the present invention provides a process for the preparation of ABC4 comprising:

a) reacting the compound of formula A5

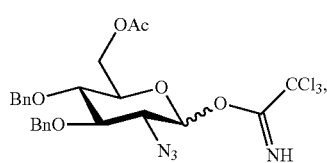

with a compound of formula BC8

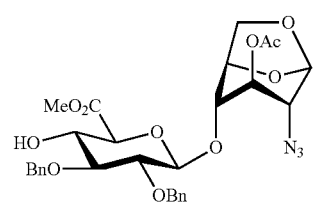

in an organic solvent in the presence of a promoter to provide a compound of formula ABC1

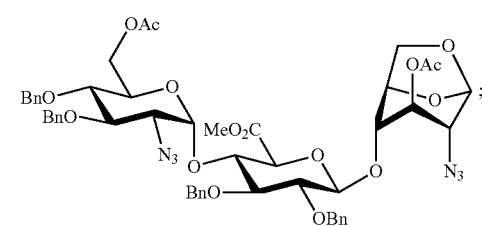

and b) converting the compound of formula ABC1 to the compound of formula ABC4

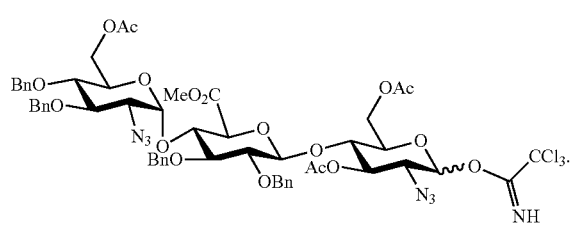

Preferably, the organic solvent used in step a) is selected from the group consisting of diethyl ether, methyl tert-butyl ether (MTBE), isopropyl ether (IPE), diglyme, toluene, xylenes and mixtures thereof. Preferably, the mixture is toluene/MTBE. More preferably, the ratio of toluene/MTBE is 0-30%. Most preferably, the ratio of toluene/MTBE is 15-25%; still more preferably about 20%.

The α/β ratio of ABC1 is improved by applying the solvent system of the present invention. For example, in toluene/MTBE, the result showed lower β form of ABC1 (4-9%) than those obtained either from toluene/IPE (12%) or toluene/diglyme (18%).

Preferably, the promoter used in step a) is trimethylsilyl trifluoromethanesulfonate (TMSOTf), triethylsilyl trifluoromethanesulfonate (TESOTf), tert-butyldimethylsilyl trifluoromethanesulfonate (TBSOTf) and mixtures thereof. The collective individual trialkylsilyl triflates or mixtures thereof are also referred to herein as 'trialkylsilyls'. More preferably, the promoter is TBSOTf.

Step (b), i.e., the conversion of ABC1 to ABC4 is described below in the detailed description section.

In still another aspect, A5

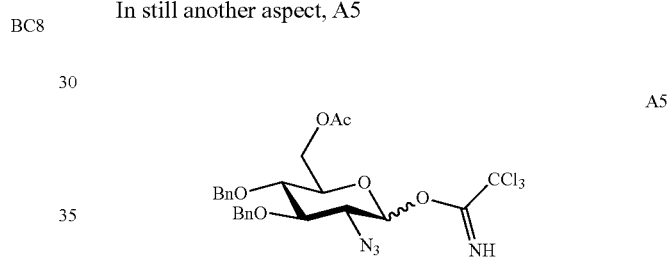

is prepared from A4

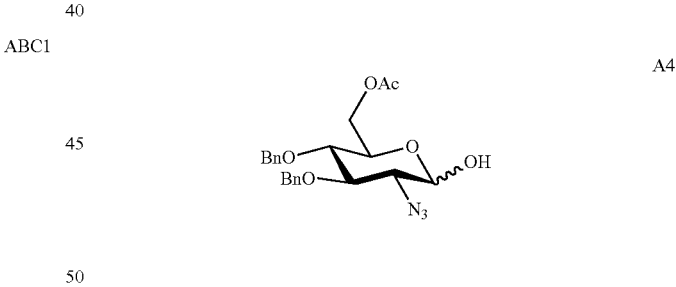

in the presence of a base and trichloroacetonitrile.

Preferably, the base is selected from alkali carbonates such as sodium carbonate or potassium carbonate. More preferably, the base is potassium carbonate.

In US application Publication No. 2012/0116066, A4 was reacted with trichloroacetonitrile and DBU to afford crude A5, after column purification, the yield was only 53%. Combining the next step wherein the product was reacted with BC8, the total yield of two steps was 34%. As provided in the present method, when DBU was replaced with an inorganic base such as $K_2CO_3$ (which can be easily filtered from organic solvent), the total yield of two steps improved to 62%.

In a fourth aspect, the present invention provides a compound of formula ABC5

ABC5

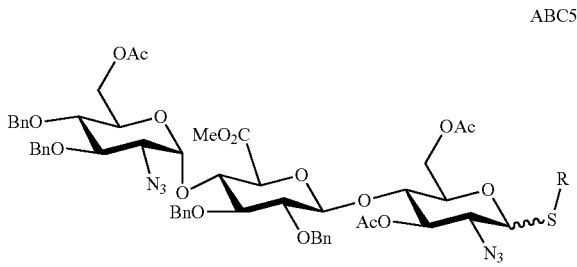

wherein R is selected from the group consisting of alkyl, phenyl, benzyl, substituted alkyl, substituted phenyl and substituted benzyl.

In particular, ABC5 is ABC5a.

ABC5a

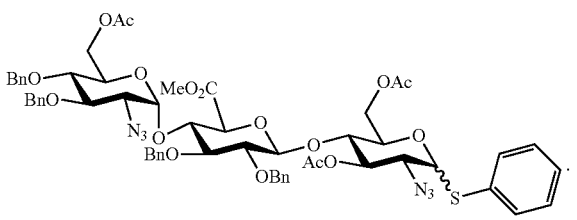

DETAILED DESCRIPTION OF THE INVENTION

I. General

Figure 1A:
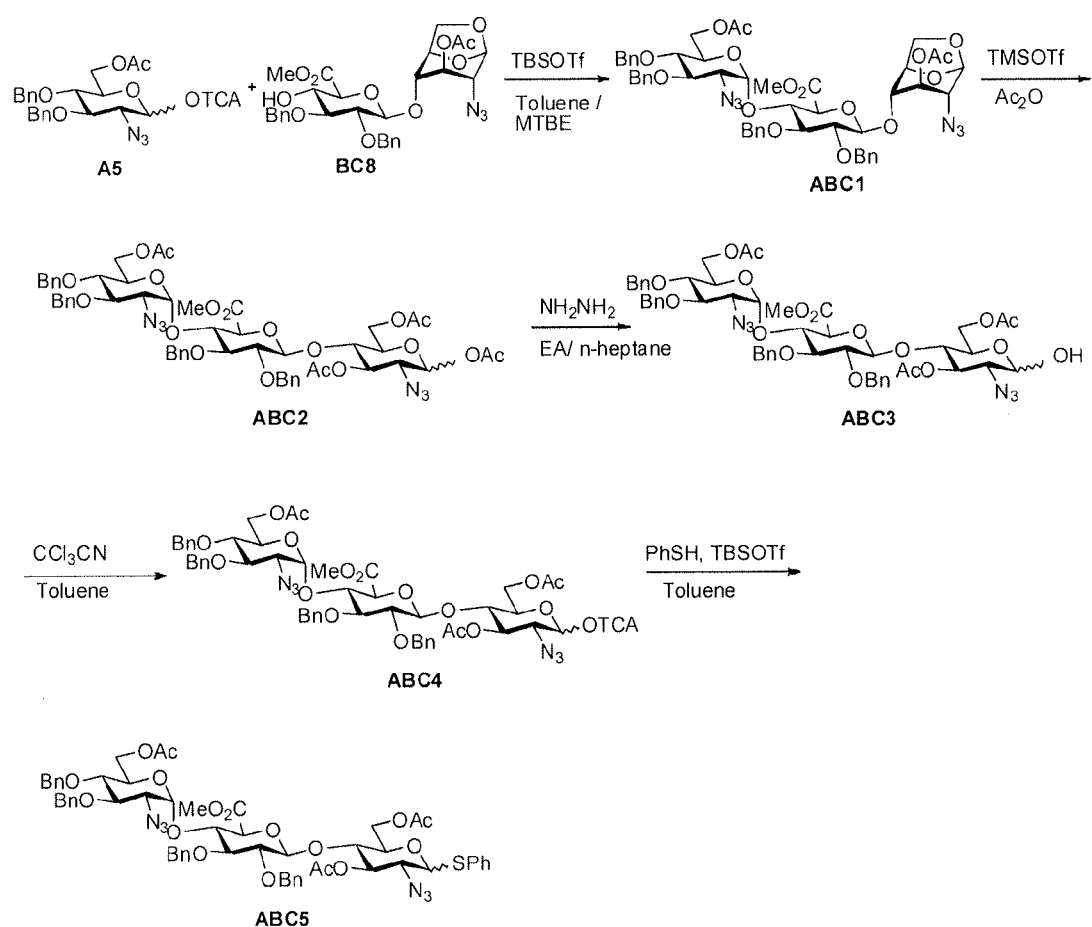
FIGS. 1A and 1B show an improved synthetic route for Fondaparinux sodium according to the present invention employing methods provided herein.
Figure 1B:
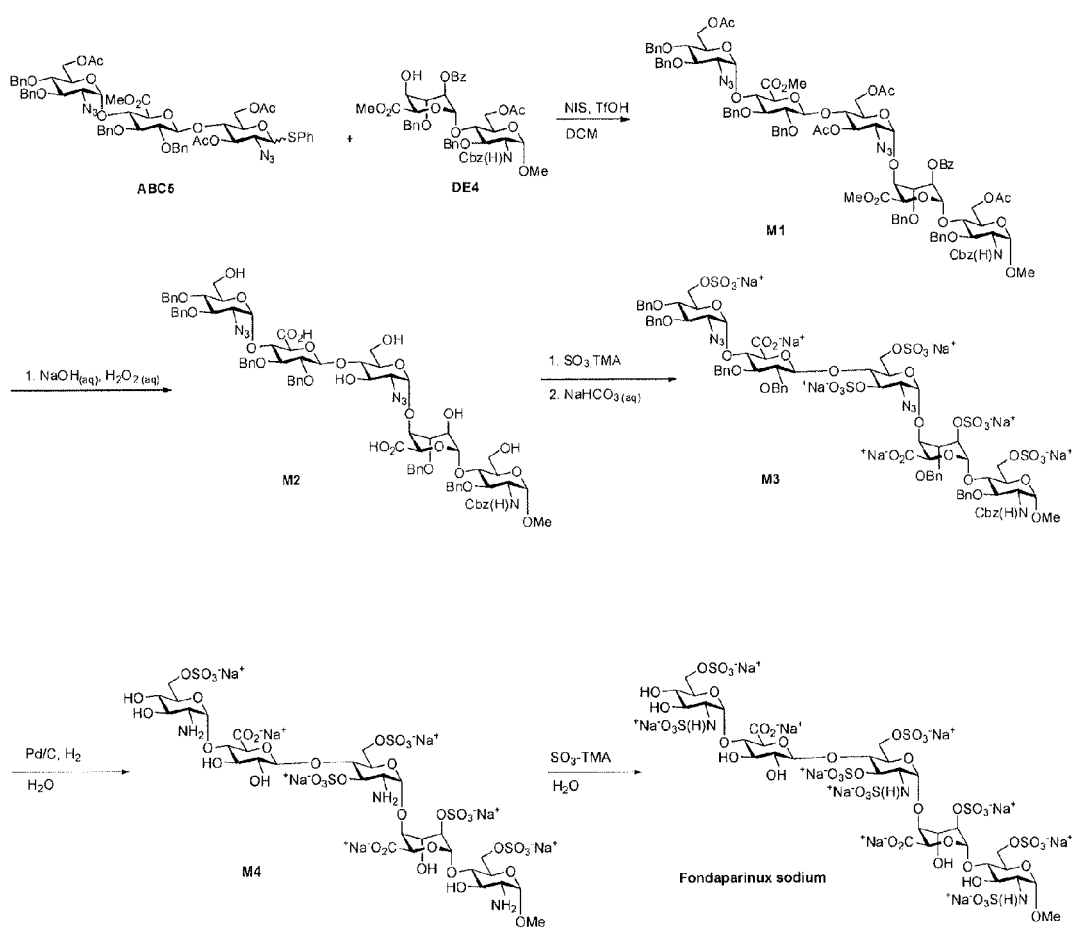

The present invention provides a process for preparation of Fondaparinux sodium. The novel processes have been discovered to be of higher yield and with reduced impurity. The process provided herein also reduces the time required to complete numerous transformations (synthetic steps).

II. Definitions

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

As used herein, the term "alkyl" by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e., $C_1$-$C_8$ means one to eight carbons), although such designators may be omitted. Unless otherwise specified, the alkyl groups of the present invention contain 1 to 12 carbon atoms. For example, an alkyl group can contain 1-2, 1-3, 1-4, 1-5, 1-6, 1-7, 1-8, 1-9, 1-10, 1-11, 1-12, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

As used herein, the term 'substituted' when referring to alkyl, phenyl and benzyl, refers to one or more substituents, typically one to three substituents that are selected to be non-interfering substituents such as halogen, amino, hydroxy, nitro, cyano, lower alkyl (e.g., $C_{1-4}$ alkyl), lower alkoxy (e.g., $C_{1-4}$ alkyl-O—), lower alkylamino (e.g., $C_{1-4}$ alkyl-NH—), di-lower alkylamino (e.g., di-$C_{1-4}$ alkylamino), and haloalkyl. One of skill in the art will appreciate that additional substituted alkyl, phenyl and benzyl are known and useful in the context of the invention.

As used herein, a solvent mixture may comprise a percentage of a first solvent in a second solvent. Unless otherwise stated, the percentage is by volume.

Various protecting groups and protecting reagents, including hydroxyl protecting reagents, are well known to one of ordinary skill in the art and include compounds that are disclosed in *Protective Groups in Organic Synthesis*, 4th edition, T. W. Greene and P. G. M. Wuts, John Wiley & Sons, New York, 2006, which is incorporated herein by reference in its entirety.

III. Embodiments of the Invention

In one aspect, the provided herein is a process for the preparation of Fondaparinux sodium of formula ABCDE5

ABCDE5

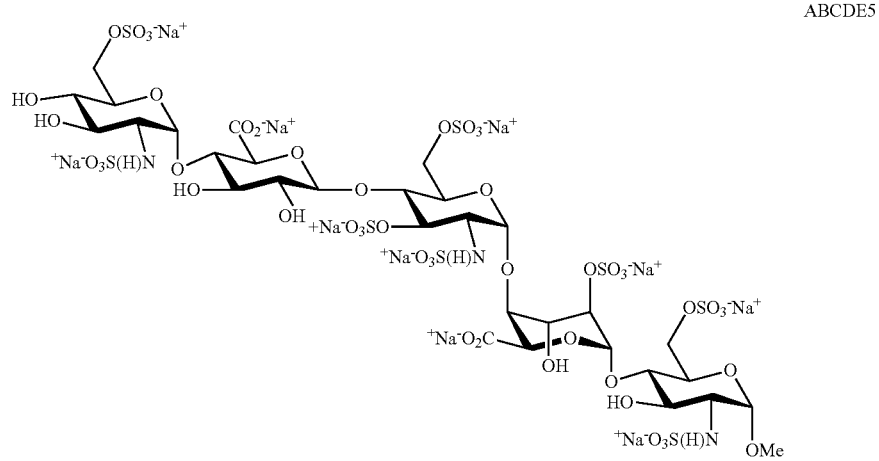

comprising contacting a compound of formula ABC5

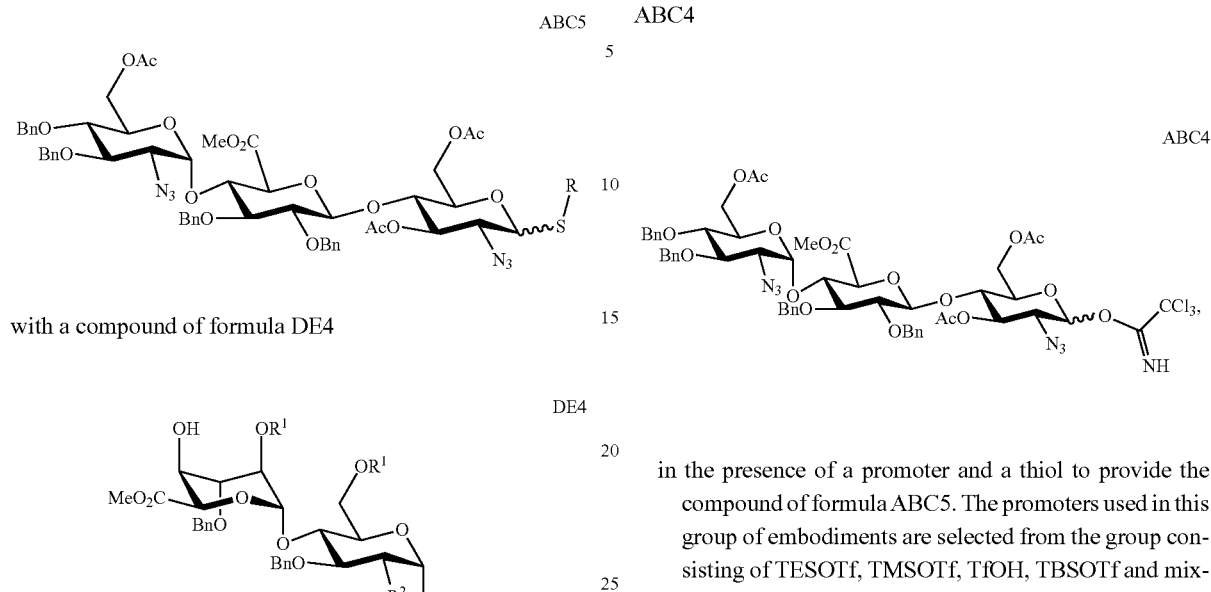

with a compound of formula DE4 to obtain a compound of formula ABCDE1

In one group of embodiments, ABC5 is obtained using a process comprising converting a compound of formula ABC4 in the presence of a promoter and a thiol to provide the compound of formula ABC5. The promoters used in this group of embodiments are selected from the group consisting of TESOTf, TMSOTf, TfOH, TBSOTf and mixtures thereof.

In another group of embodiments, ABC4 is prepared from a process comprising:

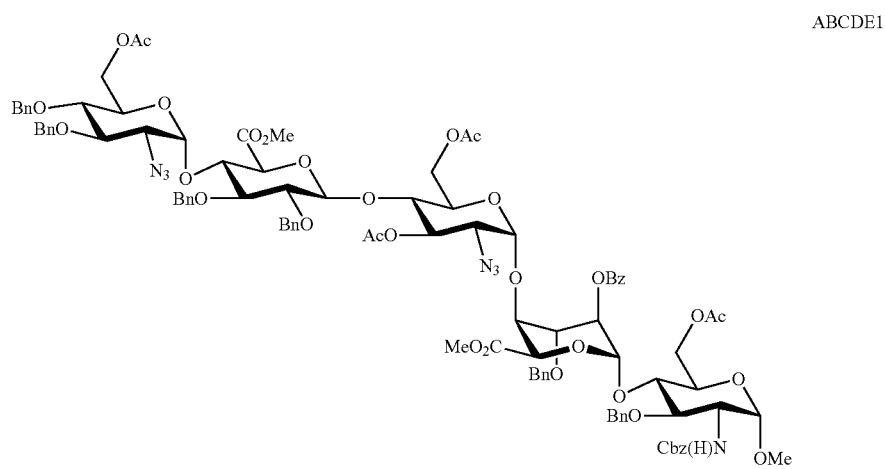

and then converting the compound of formula ABCDE1 to Fondaparinux sodium;
wherein R is selected from the group consisting of alkyl, phenyl, benzyl, substituted alkyl, substituted phenyl, substituted benzyl; $R^1$ is acetal or benzyl; and $R^2$ is azide or NHCbz.

The conversion of ABCDE1 to Fondaparinux sodium is described in more detail below.

a) converting a compound of formula A4

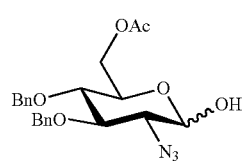

to provide a compound of formula A5

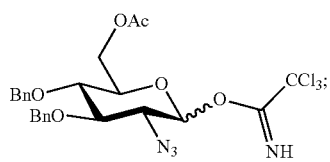

b) contacting the compound of formula A5 with a compound of formula BC8

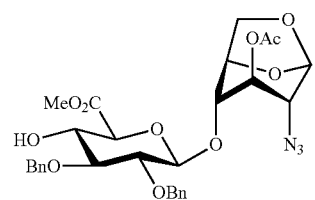

under conditions sufficient to provide a compound of formula ABC1

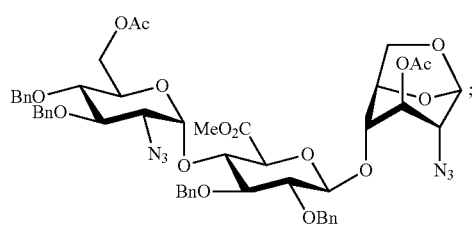

and
c) converting the compound of formula ABC1 to provide the compound of formula ABC4

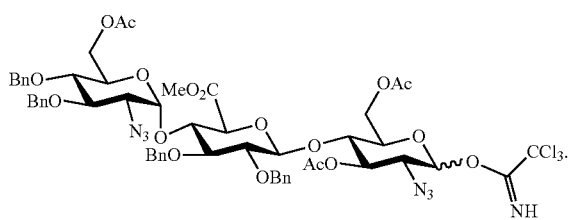

In step (a) above, the conversion of A4 to A5 is conducted in the presence of a base and trichloroacetonitrile. In one group of embodiments the base is an organic amine (e.g., DBU, pyridine, triethylamine, diisopropylethyl amine, pyrrolidine, or any other such organic base). In another group of embodiments, the base is an inorganic base (e.g., potassium carbonate, sodium carbonate, potassium bicarbonate, sodium bicarbonate, cesium carbonate, potassium phosphate, or any other such inorganic base). A number of bases are useful in this conversion, particularly DBU, potassium carbonate and mixtures thereof. Preferably the base used is an alkali base.

In step (b) above, the contacting of A5 with a compound of formula BC8 to provide a compound of formula ABC1 will generally take place in an organic solvent in the presence of a promoter. A variety of solvents are useful such as ether (e.g., diethyl ether, tetrahydrofuran), MTBE, IPE, diglyme, toluene, DCM, DCE and mixtures thereof. In one group of embodiments, the solvent is selected from diethyl ether, MTBE, IPE, diglyme, toluene, DCM and mixtures thereof. In one group of embodiments, the solvent is a mixture of 0-20% toluene or DCM in MTBE. In other embodiments, the solvent is a mixture of about 15-25% toluene in MTBE, more preferably about 20% toluene in MTBE. As with the above conversion of ABC4 to ABC5, the promoters used in this group of embodiments are selected from the group consisting of TESOTf, TMSOTf, TfOH, TBSOTf and mixtures thereof.

In step (c) above, the conversion of ABC1 to a compound of formula ABC4 will generally take place via a sequence of steps as follows. (c-1) Initially ABC1 is converted to a ketal-hydrolysed product ABC2 in the presence of a promoter, an organic solvent, a base and an acylating agent. Generally the reactions are carried out at about ambient temperature (e.g., from 20° C. to 30° C.), optionally at elevated temperatures. Suitable promoters include trialkylsilyls, trifluoromethanesulfonates, and mixtures of trialkylsilyls and trifluoromethanesulfonates. An exemplary ketal hydrolysis and anomeric acylation is provided in Example 2. (c-2) The acetyl group at the anomeric position in ABC2 is cleaved in the presence of a base and an aprotic solvent to provide compound ABC3. Examples of aprotic solvents include toluene, xylenes, THF, EA, DCM, DCE and the like. An exemplary acetyl group cleavage is described in Example 3. (c-3) A leaving group is introduced at the anomeric position of ABC3 to provide compound ABC4. Examples of suitable leaving groups include halogens, activated esters, acetimidates or the like. Generally the reaction is carried out in an aprotic solvent. Examples of aprotic solvents include toluene, xylenes, THF, EA, DCM, DCE and the like. An exemplary introduction of a trichloroacetimidate group (TCA) leaving group is provided in Example 4.

In another aspect, provided herein are novel intermediates having the formula ABC5:

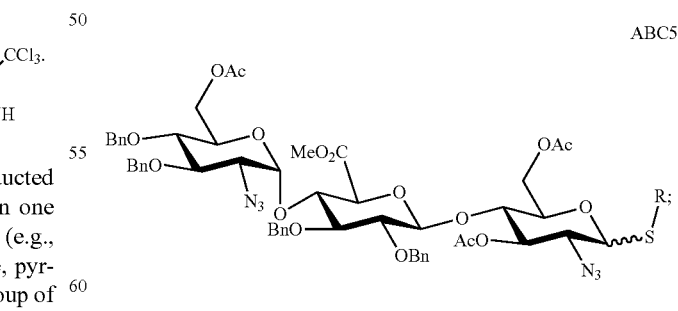

wherein R is selected from the group consisting of alkyl, phenyl, benzyl, substituted alkyl, substituted phenyl and substituted benzyl. In one group of embodiments, a compound of formula ABC5 described herein has the formula ABC5a:

ABC5a

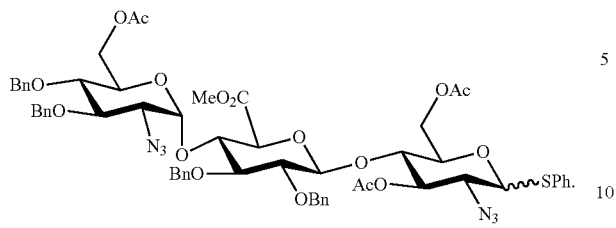

In another group of embodiments, R in ABC5 is substituted phenyl. In yet another group of embodiments, R in ABC5 is benzyl or substituted benzyl. In further embodiments, R in ABC5 is alkyl or substituted alkyl.

Also provided herein is a process for preparing Fondaparinux sodium comprising:

i) contacting the compound of formula A5

A5

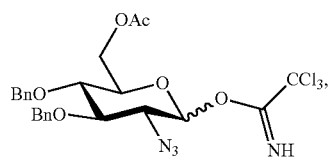

with the compound of formula BC8

BC8

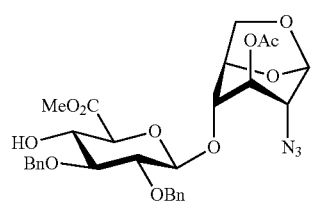

to provide the compound of formula ABC1

ABC1

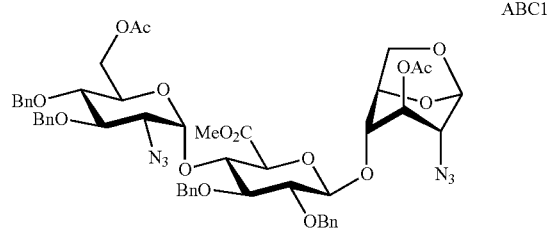

in a mixture of toluene/MTBE; and ii) converting the compound of formula ABC1 to provide Fondaparinux of formula ABCDE5:

ABCDE5

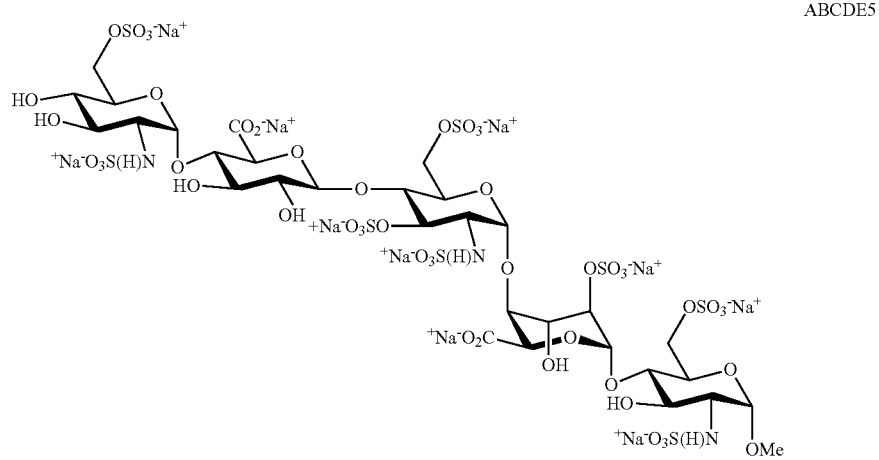

In one group of embodiments, step (i) above is conducted in toluene/MTBE in the presence of a base. In certain embodiments, the base is an organic amine (e.g., DBU, pyridine, triethylamine, diisopropylethyl amine, pyrrolidine, or any other such organic base). In another group of embodiments, the base is an inorganic base (e.g., potassium carbonate, sodium carbonate, potassium bicarbonate, sodium bicarbonate, cesium carbonate, potassium phosphate, or any other such inorganic base).

In step (ii) above, the conversion of ABC1 to ABCDE5 is achieved via a series of reactions as follows. (ii-1) Initially ABC1 is converted to a ketal-hydrolysed product ABC2 in the presence of a promoter, an organic solvent, a base and an acylating agent. Generally the reactions are carried out at about ambient temperature (e.g., from 20° C. to 30° C.), optionally at elevated temperatures. Suitable promoters include trialkylsilyls, trifluoromethanesulfonates, and mixtures of trialkylsilyls and trifluoromethanesulfonates. An exemplary ketal hydrolysis and anomeric acylation is provided in Example 2. (ii-2) The acetyl group at the anomeric position in ABC2 is cleaved in the presence of a base and an aprotic solvent to provide compound ABC3. Examples of aprotic solvents include toluene, xylenes, THF, EA, DCM, DCE and the like. An exemplary acetyl group cleavage is described in Example 3. (ii-3) A leaving group is introduced at the anomeric position of ABC3 to provide compound ABC4. Examples of suitable leaving groups include halogens, activated esters, acetimidates or the like. Generally the reaction is carried out in an aprotic solvent. Examples of aprotic solvents include toluene, xylenes, THF, EA, DCM, DCE and the like. An exemplary introduction of a trichloroacetimidate group (TCA) leaving group is provided in Example 4. (ii-4) A thio-donor compound ABC5 is generated from ABC4 by reaction of ABC4 with a thiol in the presence of a promoter in an organic solvent. Generally the reaction is carried out in an aprotic solvent. Examples of aprotic solvents include toluene, xylenes, THF, EA, DCM, DCE and the like. Suitable promoters include trialkylsilyls, trifluoromethanesulfonates, and mixtures of trialkylsilyls and trifluoromethanesulfonates. An exemplary introduction of a thiophenyl group is described in Example 4. Generally the reaction mixture includes a base. Examples of bases include organic bases such as triethylamine, diisopropylamine, diisopropylethylamine and the like, or inorganic bases such as potassium carbonate, sodium carbonate, cesium carbonate and the like. One of skill in the art will understand that the introduction of a thio-donor moiety is possible under various conditions and depends on the leaving group present in the compound. (ii-5) The thio donor compound ABC5 is reacted with an acceptor compound such as DE4 to obtain an oligosaccharide ABCDE1. The reaction is carried out in the presence of a radical initiator and/or a promoter in an organic solvent. Generally the reaction is carried out in an aprotic solvent. Examples of aprotic solvents include toluene, xylenes, THF, EA, DCM, DCE and the like. The reaction is generally carried out at a temperatures ranging from about −30° C. to about 40° C. Suitable promoters include trialkylsilyls, trifluoromethanesulfonates, and mixtures of trialkylsilyls and trifluoromethanesulfonates. Non-limiting examples of radical initiators include N-iodosuccinimide, N-bromosuccinimide and the like. An exemplary reaction between a donor and an acceptor compound is shown in Example 5. One of skill in the art will understand that the donor-acceptor reaction is possible under various conditions and depends on the thio-donor moiety and the acceptor moiety present in the compounds.

The conversion of ABCDE1 to ABCDE5 is achieved as follows. (ii-6) The ester group in ABCDE1 is cleaved in the presence of a peroxide and a base in an aprotic solvent to provide ABCDE2. Examples of aprotic solvents include toluene, xylenes, THF, EA, DCM, DCE and the like. The reaction is generally carried out initially at temperatures below 10° C., then warmed to ambient temperature (e.g., 20° C. to 30° C.). Example 6 provides an exemplary procedure for ester cleavage in an oligosaccharide. (ii-7) ABCDE2 is then 0-sulfated in the presence of a base to provide ABCDE3. The reaction is generally carried out in an aprotic solvent by introduction of sulfate groups using a sulfating reagent, followed by addition of a base to introduce counterions for the sulfate groups. Example 7 provides an exemplary procedure for introduction of sodium sulfate groups. (ii-8) The Cbz protecting group in ABCDE3 is removed under suitable conditions to provide ABCDE4. In some cases, hydrogenation is used which also reduces the azido groups to amine groups. The hydrogenation is typically carried out at ambient temperatures (e.g., 20° C. to 30° C.) for a period of 1-5 days, preferably 1-3 days. Example 8 provides an exemplary procedure for conversion of ABCDE3 to ABCDE4. (ii-9) ABCDE4 is converted to Fondaparinux via an N-sulfation step, using a sulfating reagent, followed by addition of a base to introduce counterions for the sulfate groups. The compound is then desalted. Example 9 provides an exemplary procedure for introduction of sodium sulfate groups. The sodium salt is desalted in the final step to obtain Fondaparinux.

In a select group of embodiments, a solvent mixture for the reaction of A5 with BC8 in step (i) above is a toluene/MTBE mixture having a ratio of toluene/MTBE from 10% to 30%, or from 15% to 25%, preferably 20%.

EXAMPLES

The following examples are presented to describe the invention in further detail. However, the present invention is by no means restricted to the specific embodiments described herein. The following abbreviations are used in the specification, and examples: DCM is dichloromethane; EA is ethyl acetate; THF is tetrahydrofuran; MTBE is methyl tert-butyl ether; DMAc is dimethylacetamide; OTCA is a trichloroacetimidate group; DCE is dichloroethane; IPE is isopropyl ether; CBz is carboxybenzyl, a carbamate protecting group. Compound BC8 can be prepared according to U.S. application publication no. 20120083594. Compound A4 can be prepared according to procedures in *J. Am Chem Soc.*, 2005, 127, 3767-3773; or Tetrahedron: Asymmetry, 2005, 16(2), 411-424.

Example 1

Preparation of ABC1

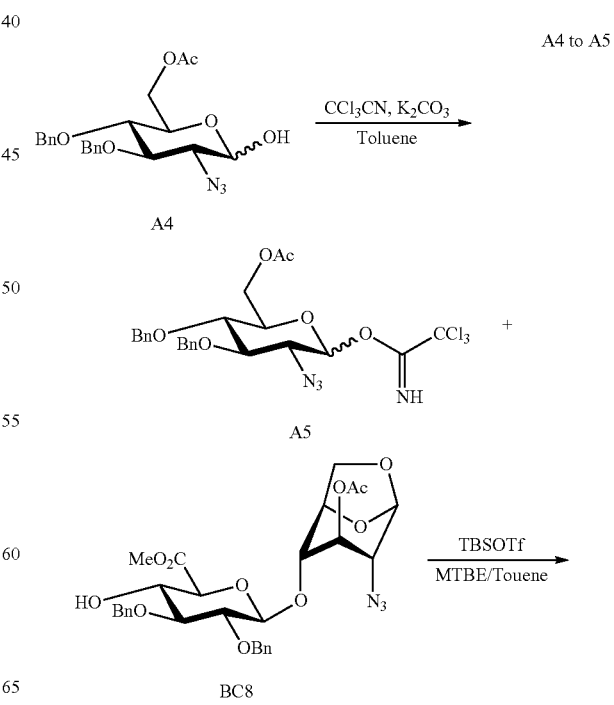

-continued

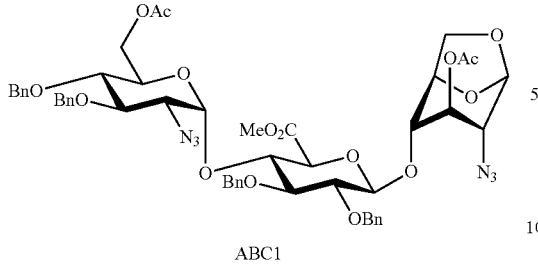

ABC1

A four-necked round bottom flask was equipped with a mechanical stirrer and a thermometer. To the flask was added A4 (32 g, 75 mmol, 1.4 equiv), toluene (64 mL), $K_2CO_3$ (52 g, 374 mmol, 7.0 equiv), and $CCl_3CN$ (37 mL, 374 mmol, 7.0 equiv) at 20-30° C. under nitrogen. The mixture was stirred at 20-30° C. for 4 hr. The mixture was filtered and the filtered cake was washed with toluene (64 mL). The filtrate and washing were combined to afford A5 in toluene solution. After being cooled to no more than −10° C., the A5/toluene solution was ready to be used.

BC8 to ABC1

A four-necked round bottom flask was equipped with a mechanical stirrer and a thermometer. To this flask was added BC8 (32 g, 53 mmol, 1 equiv) and MTBE (576 mL) at 20-30° C. under nitrogen. The mixture was heated to no more than 45° C. for dissolution. After being cooled to 20-30° C., 3 Å molecular sieves (15 g) were added to the mixture and the resulting mixture was stirred at this temperature for 2 hr. The mixture was then cooled to −35 to −25° C. TBSOTf (5 mL, 21 mmol, 0.4 equiv) was added at −35 to −25° C., and the mixture was stirred at this temperature for about 15 min. The resulting mixture containing BC8 and 3 Å molecular sieves in MTBE was ready to be used.

To the flask containing A5/toluene solution was added into the mixture containing BC8 and 3 Å molecular sieves in MTBE over 30 min while maintaining temperature at −35 to −25° C. The mixture was stirred at −35 to −25° C. for 1 hr. Triethylamine (23 mL, 160 mmol, 3 equiv) and $Ac_2O$ (5 mL, 53 mmol, 1 equiv) were successively added at −35 to −25° C. The mixture was heated to about 50° C. and stirred for 6 hr. The mixture was filtered and the filtered cake was washed with MTBE (64 mL). The filtrate and washing were combined and concentrated to afford crude ABC1 solution. Crude ABC1 solution was purified using column chromatography (silica gel; eluting solvent: EtOAc/n-heptane (first eluting solvent is 1:4 and then 2:3)) and then concentrated to afford ABC1 solution (50 g, 88%) in EtOAc/n-heptane (1/1(v/v)).

Example 2

Preparation of ABC2

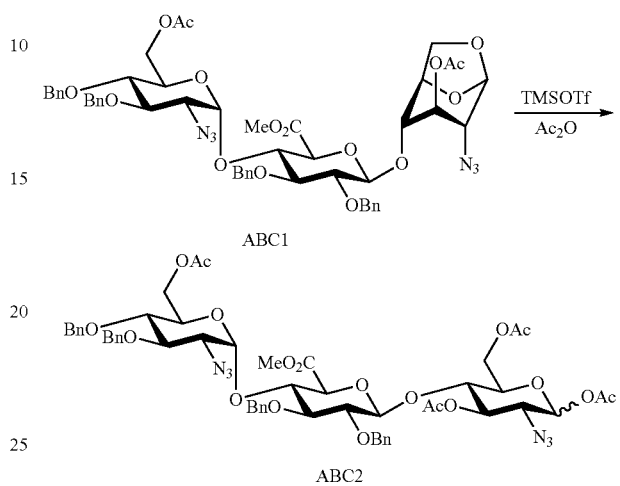

A three-necked round bottom flask was equipped with a mechanical stirrer and a thermometer. To the flask was added the previously reserved ABC1 in EtOAc/n-heptane solution (162 mL, 1/1(v/v)) at 20-30° C. under nitrogen. After the mixture was cooled to 0-10° C., $Ac_2O$ (16.3 g, 0.16 mol, 3.0 equiv) and TMSOTf (3.6 g, 0.02 mol, 0.3 equiv) were successively added at this temperature. The mixture was stirred at 0-10° C. for not less than 10 hr. Triethylamine (45 mL, 0.27 mol, 6.0 equiv) was slowly added at 0-10° C. The mixture was stirred at 0-10° C. for 1 hr. 20% $NaCl_{(aq)}$ (64 mL, 2 vol) was slowly added at 0-10° C. The mixture was stirred for 2 hr. The separated aqueous portion was discarded. The separated organic portion containing ABC2 in EtOAc/n-heptane (1/1 (v/v)) solution was ready to be used in the next step.

Example 3

Preparation of ABC3

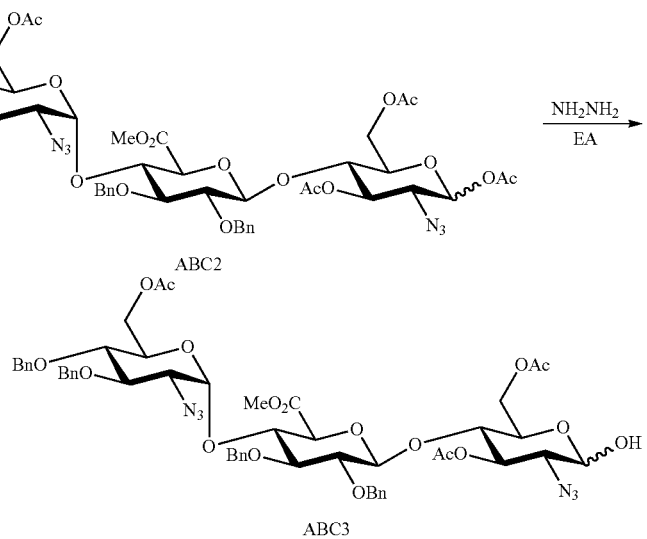

A three-necked round bottom flask was equipped with a mechanical stirrer and a thermometer. To the flask was added the previously reserved ABC2 in EtOAc/n-heptane (1/1 (v/v)) solution at 20-30° C. under nitrogen. H₂NNH₂—H₂O (3.8 g, 80 mmol, 1.4 equiv) was added at 20-30° C., and the mixture was stirred at this temperature for 3 hr. A 5% solution of NaCl$_{(aq)}$ (160 mL) was added at 20-30° C., and the mixture was stirred at this temperature for 1 hr. The stirring was stopped for phase separation. The separated aqueous phase was discarded. The organic and emulsion portions were combined and concentrated to afford crude ABC3 in EtOAc/n-heptane solution. Crude ABC3 solution was purified with column chromatography (silica gel; eluting solvent: acetone/toluene (containing 0.05%(v/v) of Et₃N, 5/95(v/v))) and then concentrated to afford ABC3 in toluene solution (44 g, 94%).

Example 4

Preparation of ABC5 at 20-30° C. The mixture was stirred at 20-30° C. for not less than 4 hr. The mixture was filtered and the filtered cake was washed with toluene (64 mL, 2 vol). The filtrate and washing were combined to afford ABC4 in toluene solution. After being cooled to no more than −5° C., the ABC4/toluene solution (about 160 mL, 5 vol) was ready to be used.

ABC4 to ABC5

A four-necked round bottom flask was equipped with a mechanical stirrer and a thermometer. To the flask was added thiophenol (24 g, 0.2 mmol, 4 equiv) and toluene (260 mL) at 20-30° C. under nitrogen. The mixture was cooled to −20 to −10° C. TBSOTf (21 g, 0.08 mol, 1.5 equiv) was added at −20 to −10° C. The resulting mixture containing thiophenol and TBSOTf in toluene was ready to be used.

To the flask containing ABC4 solution was added the mixture containing thiophenol and TBSOTf in toluene over 30 min while maintaining temperature at −20 to −10° C. The mixture was stirred at −20 to −10° C. for 2 hr. Et₃N/toluene

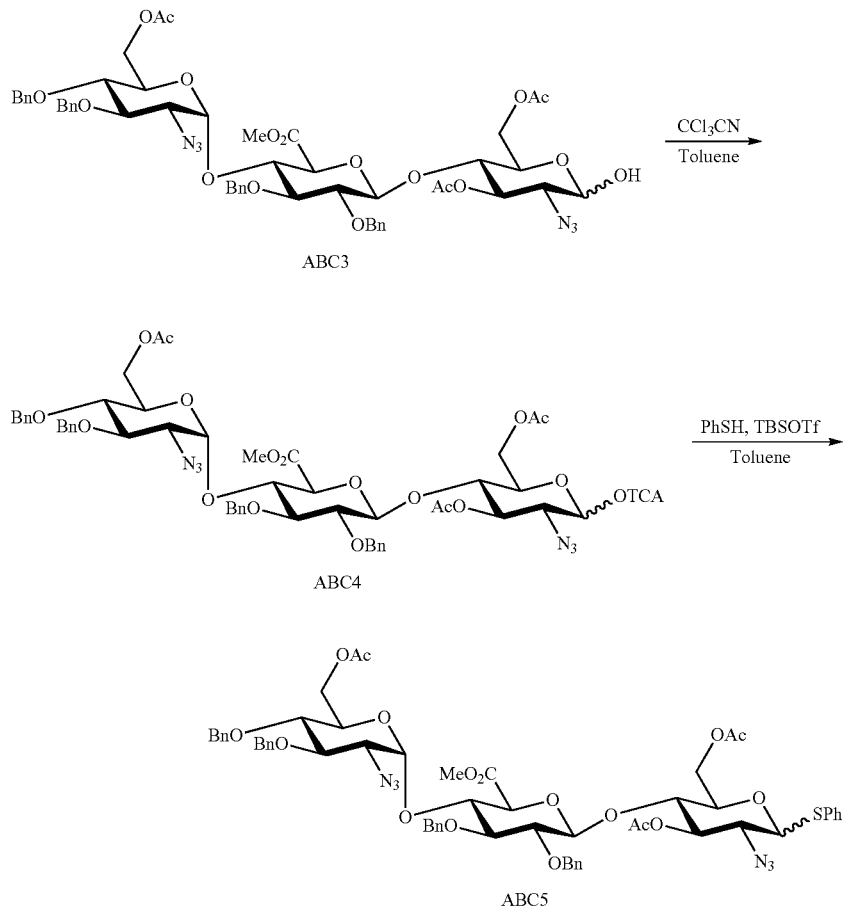

ABC3 to ABC4

A four-necked round bottom flask was equipped with a mechanical stirrer and a thermometer. To the flask was added ABC3/toluene solution (about 96 mL, 3 vol) at 20-30° C. under nitrogen. K₂CO₃ (74 g, 0.53 mol, 10 equiv) and CCl₃CN (77 g, 0.53 mol, 10 equiv) were successively added (15 mL/65 mL) was slowly added over about 30 min while maintaining temperature no more than −5° C. The mixture was stirred at no more than −5° C. for 30 min. The mixture was concentrated to afford crude ABC5 solution in toluene. ABC5 solution was purified with column (silica gel; eluting solvent: EtOAc/toluene (containing 0.05% (v/v) of Et₃N, 2/98, (v/v))) to afford ABC5 in toluene solution (42 g, 88%).

Example 5

Preparation of ABCDE1

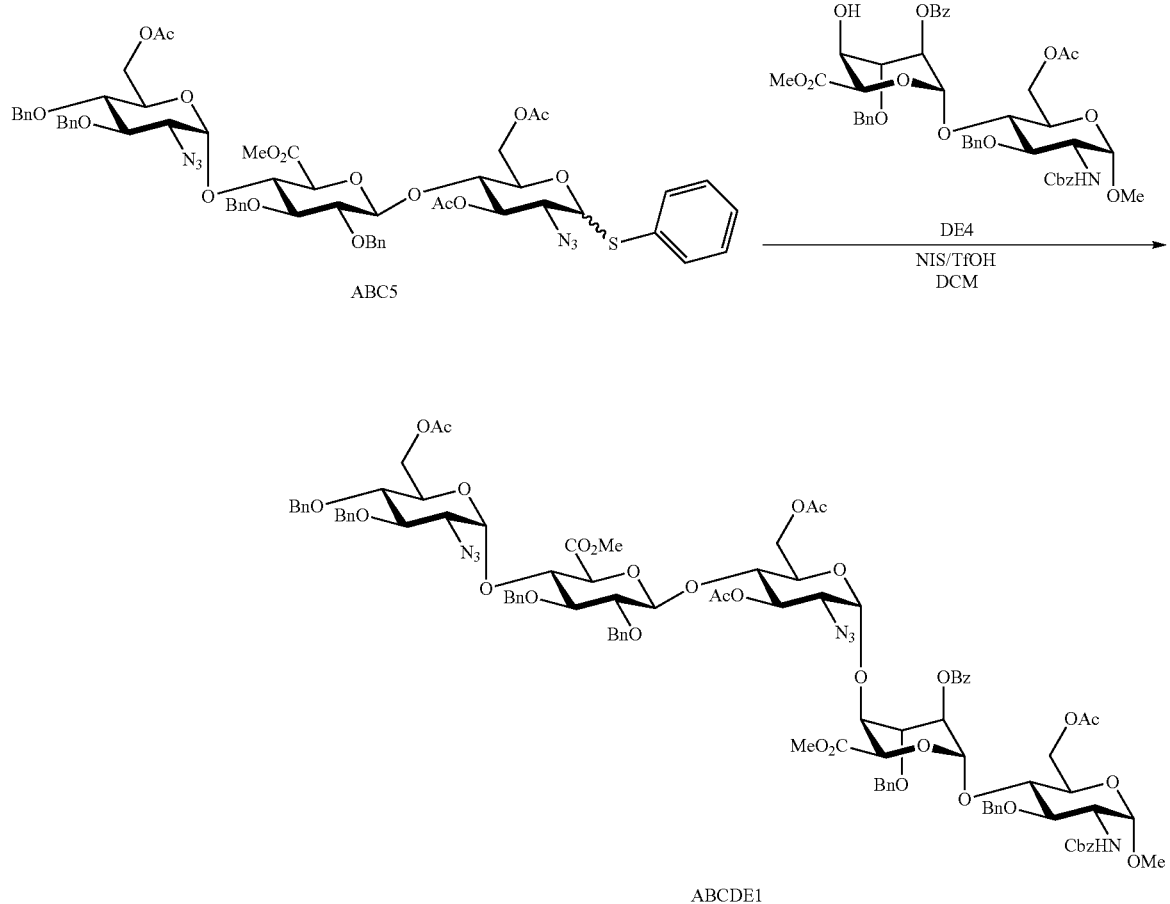

ABC5 (35 g, 0.03 mol, 1.0 equiv), DE4 (28 g, 0.033 mol, 1.1 equiv), and DCM (700 g,) were added into a four-necked round bottom flask equipped with a mechanical stirrer and a thermometer at 20-40° C. under nitrogen. The mixture was stirred at 20-40° C. for 30 min to obtain a homogeneous solution. 3 Å molecular sieves (35 g) was added at 20-40° C., and the mixture was stirred at this temperature for 1 hr.

After the mixture was cooled to −30 to −20° C., N-iodosuccinimide (NIS) (10.2 g, 1.5 equiv, 0.045 mol) was added at this temperature and stirred for 15 min. TfOH (1.8 g, 0.012 mol, 0.4 equiv) in DCM (10 mL) was slowly added at −30 to −20° C., and the mixture was stirred at this temperature for 2 hr. Et$_3$N (6.1 g, 0.06 mol, 2 equiv) was added at −30 to −20° C., and the mixture was stirred at this temperature for 30 min. The mixture was filtered through a celite pad, and the filtered cake was washed with DCM (140 mL). The combined filtrate and washing was added 30% Na$_2$S$_2$O$_3$.5H$_2$O$_{(aq)}$ (105 mL, 3 vol) at 20-40° C. After the mixture was stirred at 20-40° C. for 1 hr, the stirring was stopped for about 5 min to effect phase separation. The separated aqueous portion was discarded. The separated organic portion was concentrated to afford crude ABCDE1 solution in DCM. Crude ABCDE1 solution was purified with column chromatography (silica gel; eluting solvent: EtOAc/toluene (containing Et$_3$N (0.1% (v/v)) 1/9(v/v)) to provide a solution of ABCDE1 in toluene solution.

ABCDE1 in toluene solution (about 105 mL) was added into a four-necked round bottom flask equipped with a mechanical stirrer and a thermometer under nitrogen. After the mixture was heated to 35-45° C., IPA (105 mL) and n-heptane (105 mL) were sequentially added at this temperature. ABCDE1 seed (0.035 g) was added at 35-45° C., and the mixture was stirred at this temperature for 1 hr. After n-heptane (175 mL) was added at 35-45° C., the mixture was cooled to 15-25° C. and stirred for 1 hr. The mixture was filtered and the filtered cake was washed with n-heptane (70 mL). The wet cake was dried at no more than 60° C. to afford ABCDE1 (39 g, 65%) as a white solid.

Example 6

Preparation of ABCDE2

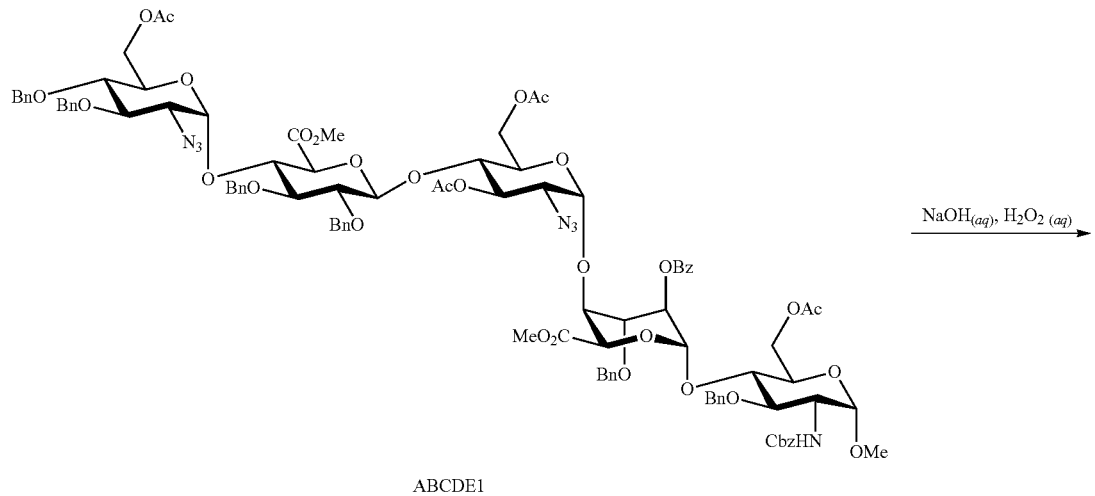

ABCDE1

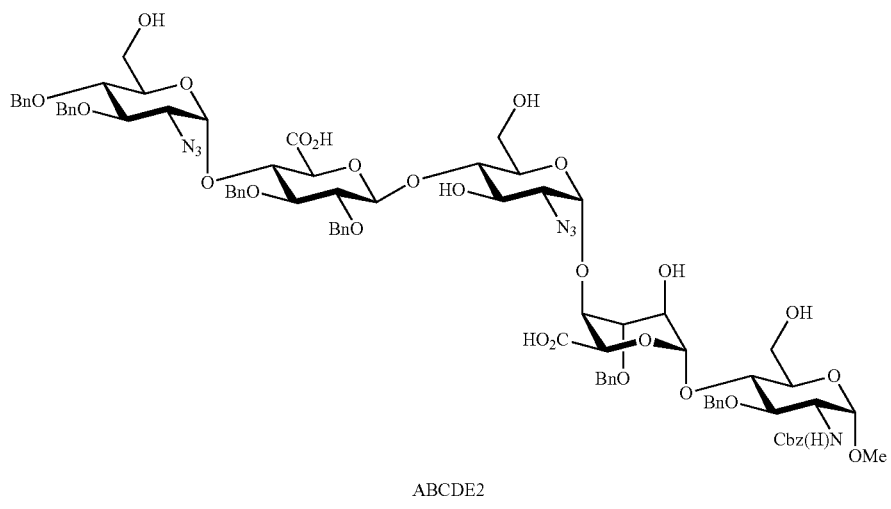

ABCDE2

THF (250 mL) and ABCDE1 (50 g, 26.4 mmol, 1.0 equiv) were charged into a four-necked round bottom flask at 20-40° C. under nitrogen. The mixture was cooled to 10° C., and 35% $H_2O_{2(aq)}$ (102.5 mL, 1161 mmol, 44 equiv) was added at this temperature. 2N $NaOH_{(aq)}$ (356 mL, 712.4 mmol, 27 equiv) was added at 10° C. The mixture was heated to 20-30° C. and stirred for 48 hr. The stirring was stopped for about 5 min to affect phase separation. The separated organic portion was saved, and the separated aqueous portion was discarded. The reserved organic portion was added 30% $Na_2S_2O_3 \cdot 5H_2O_{(aq)}$ (250 mL, 5 vol), and the mixture was stirred for about 5 min. The stirring was stopped for about 5 min to affect phase separation. The separated organic portion was saved, and the separated aqueous portion was discarded. The reserved organic portion was added 30% $Na_2S_2O_3 \cdot 5H_2O_{(aq)}$ (250 mL, 5 vol), and the mixture was stirred for about 5 min. The stirring was stopped for about 5 min to affect phase separation. The separated organic portion was saved, and the separated aqueous portion was discarded. The reserved organic portion was added $H_2O$ (500 mL, 10 vol), and 1N $HCl_{(aq)}$ (45 mL, 0.9 vol) was added till pH of the mixture reached 4-5. Acetone (250 mL, 5 vol) was added and the mixture was concentrated at 35-60° C. to a volume of about 700 mL. 1N $HCl_{(aq)}$ (5 mL) was added to reach a pH of the mixture of about 2.5-3.5. After being stirred at 20-30° C. for 30 min, the mixture was filtered and the filtered cake was washed with $H_2O$ (250 mL). The wet cake was dried at no more than 60° C. to afford ABCDE2 as white solid (38.4 g, 82% yield).

Example 7

Preparation of ABCDE3

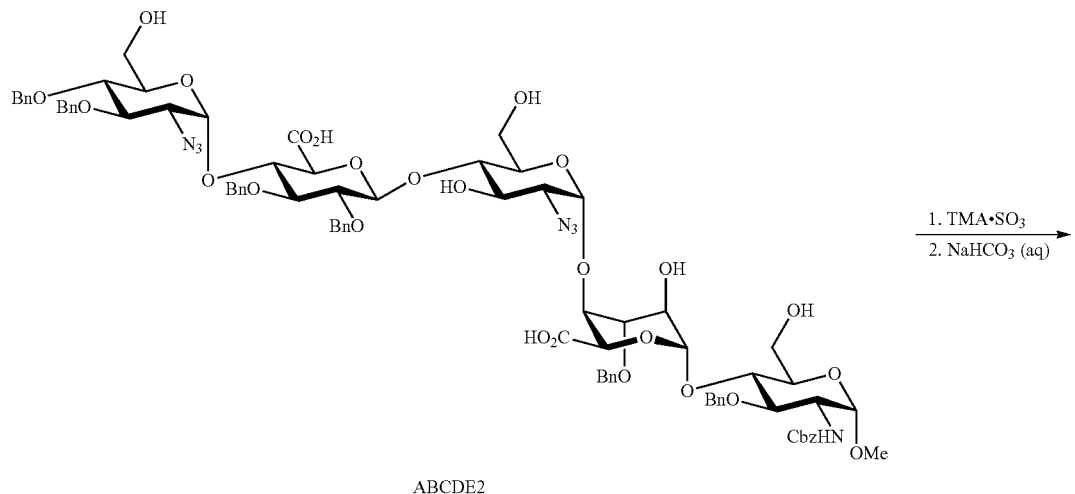

ABCDE2

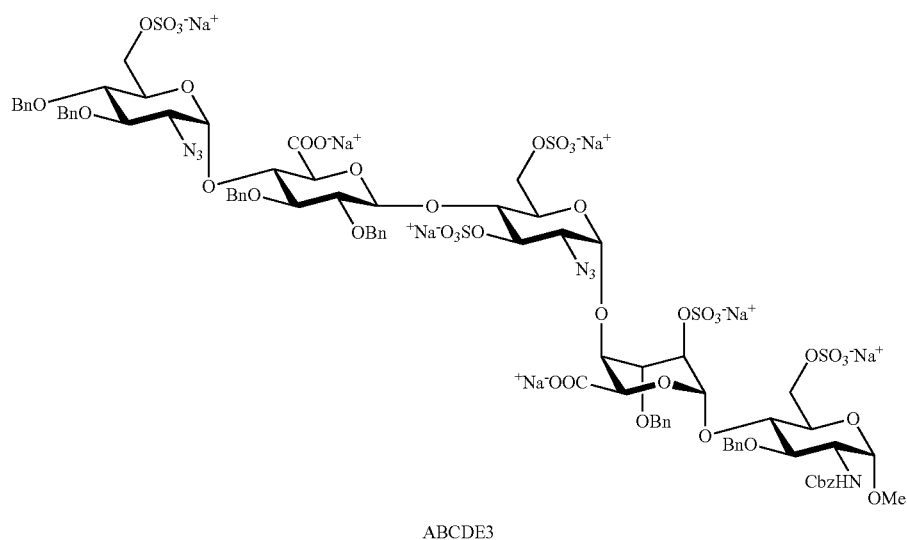

ABCDE3

ABCDE2 (8 g, 1.0 equiv, 5.02 mmol), SO$_3$-TMA complex (38.4 g, 55 equiv, 275.92 mmol), and DMAc (88 mL) were added into a round bottom flask equipped with a mechanical stirrer and a thermometer under nitrogen at 20-40° C. The slurry mixture was heated to 55-65° C. and stirred for 6 hr. After being cooled to no more than 10° C., to the mixture was added 8% NaHCO$_{3(aq)}$ (40 mL) at no more than 30° C. The mixture was filtered and the filtered cake was washed with DMAc (96 mL). After the combined filtrate and washing was cooled to no more than 10° C., water (88 mL) was slowly added while maintaining temperature at 30° C. A mixture containing crude ABCDE3 solution DMAc/water was thus obtained. ABCDE3 was purified with HP20SS resin by eluting solvent via NaCl$_{(aq)}$ (10%) and then MeOH and then solvent exchanged by water to afford ABCDE3 aqueous solution.

Example 8

Preparation of ABCDE4

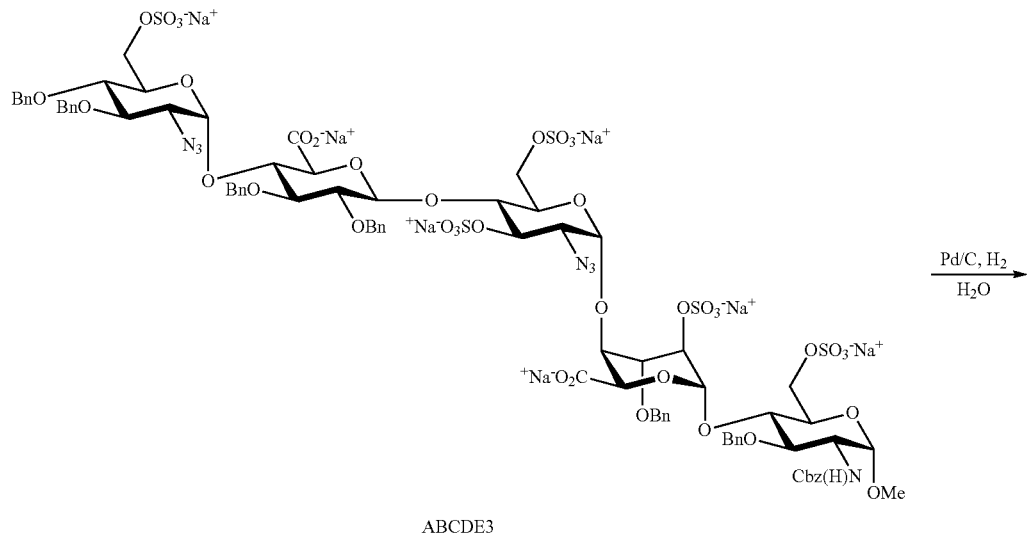

ABCDE3

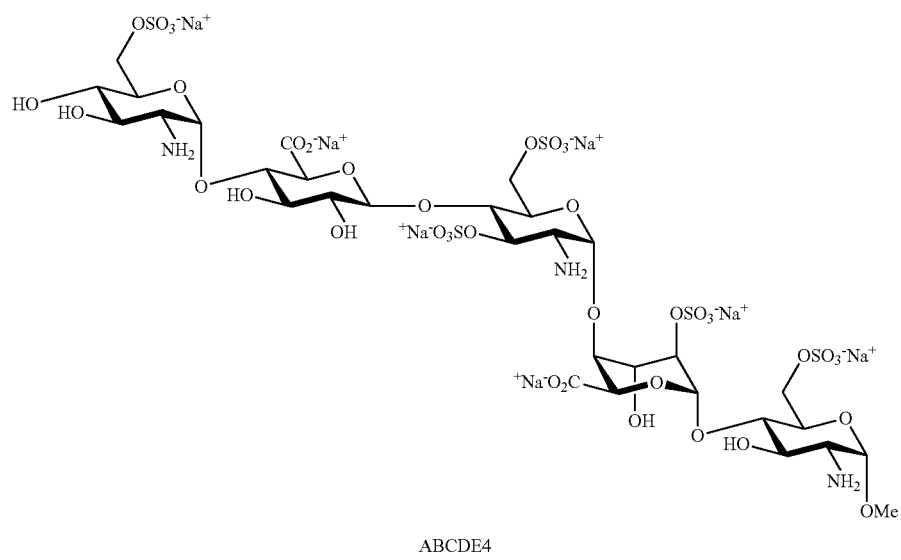

ABCDE4

ABCDE3 aqueous solution (based on 8 g of ABCDE2), and 10% Pd/C (3.2 g, 40% wt) were added into an autoclave at 20-30° C. The mixture was exposed to hydrogen (0-0.5 kg, gauge pressure) at 20-30° C. for 48 hr. The mixture was filtered through a celite pad, and the filtered cake was washed with water (32 mL). After the combined filtrate and washing was added activated charcoal (1.6 g,) at 20-30° C., the mixture was stirred at this temperature for 3 hr. The mixture was filtered through a celite pad, and the filtrate was saved. The reactor was rinsed with PPW (32 mL), and the solution was filtered through a 0.2 micrometer filter. The two filtrates were combined to afford a ABCDE4 aqueous solution.

Example 9

Preparation of Fondaparinux

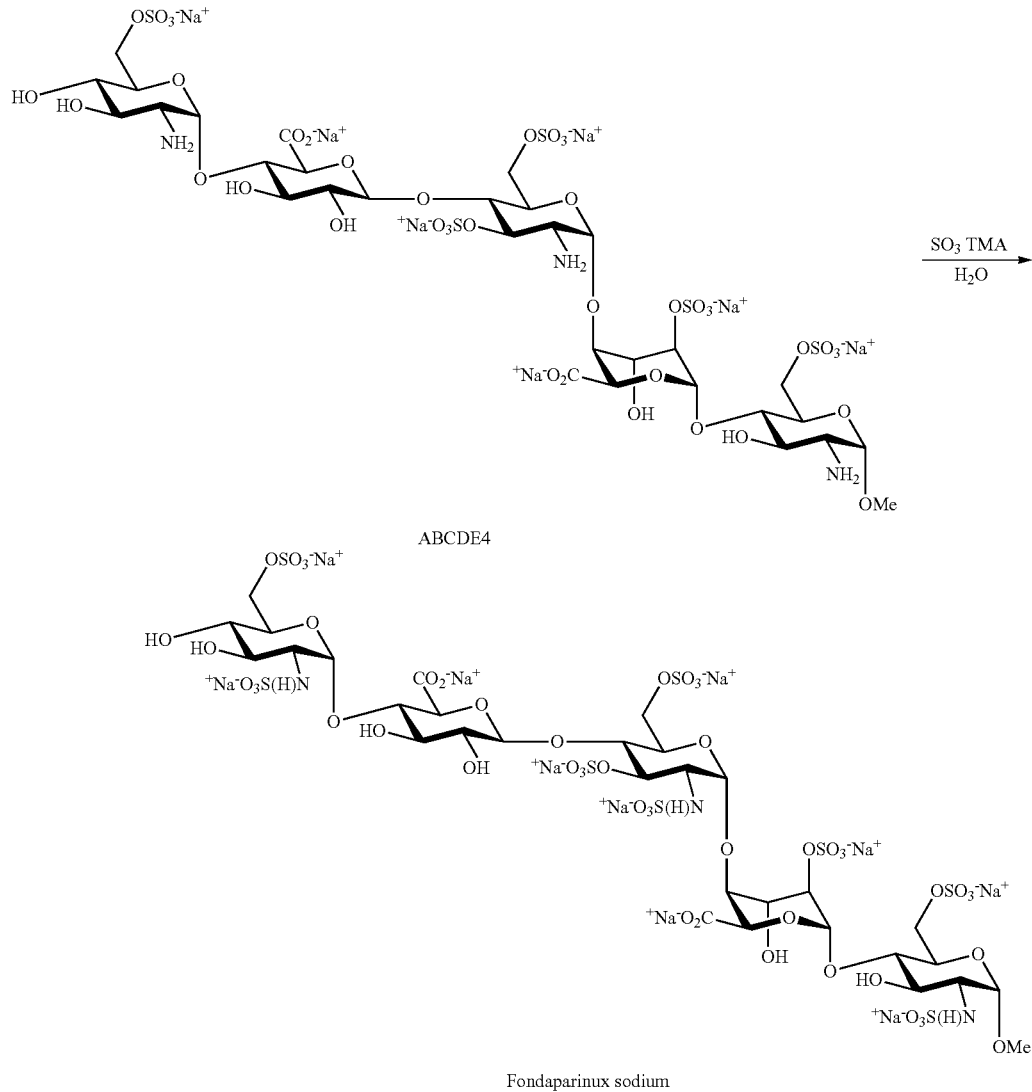

ABCDE4 aqueous solution (based on 8 g of ABCDE2) was added into a round bottom flask equipped with a mechanical stirrer and thermometer at 20-40° C. The mixture was added 1N HCl$_{(aq)}$ till pH reached 8-9. After SO$_3$.TMA (23.04 g, 33 equiv, 165.5 mmol) was added at 20-40° C., the mixture was heated to 40-50° C. and stirred for 10 hr. The mixture was cooled to no more than 10° C. The mixture was filtered and the filtered cake was washed with water (32 mL). The filtrate was added 1N NaOH$_{(aq)}$ till pH reached 9-10. The mixture was heated to 45-55° C. and stirred for 20 hr. The mixture was cooled to no more than 30° C. A mixture containing crude Fondaparinux sodium aqueous solution was thus obtained.

Crude Fondaparinux sodium aqueous solution (2.4 g) was purified with Q Sepharose Fast Flow resin (QSFF) (190 mL) using the eluting solvent via 0.4M NaCl$_{(aq)}$, 0.8M NaCl$_{(aq)}$ and 2M NaCl$_{(aq)}$ to afford Fondaparinux sodium solution. Fondaparinux sodium was desalted by 0.1 m$^2$ of 1 kDa regenerous cellulose (RC) membrane using Tangential Flow Filtration (TFF) and then lyophilized to afford Fondaparinux (2.2 g, 80%).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A process for preparing ABC1 comprising:
i) contacting the compound of formula A5

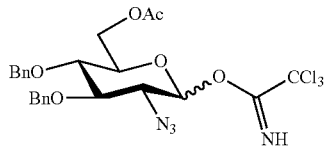

A5 with the compound of formula BC8

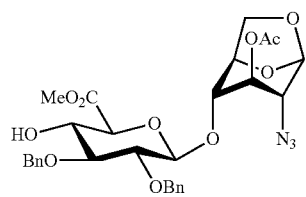

BC8 to provide the compound of formula ABC1

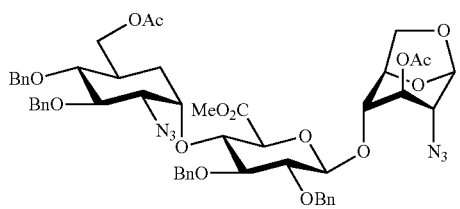

ABC1 in a solution containing toluene and an organic solvent, which is selected from the group consisting of diethyl ether, methyl tert-butyl ether (MTBE), isopropyl ether, diglyme, and mixtures thereof.

2. The process of claim 1, wherein the solution is 0-20% toluene in methyl tert-butyl ether (MTBE) by volume of solvent mixture.

3. The process of claim 1, further comprising
ii) converting the compound of formula ABC1 in the presence of a promoter and an acylating agent to a compound of formula ABC2

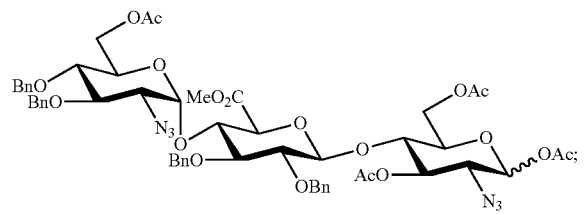

ABC2 iii) converting the compound of formula ABC2 in the presence of a base to the compound of formula ABC3

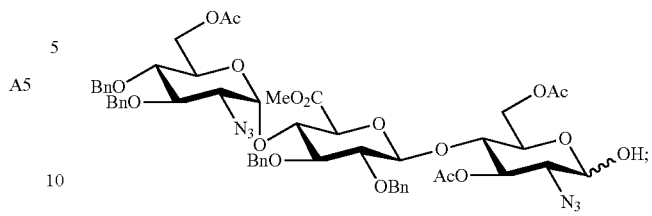

ABC3 iv) converting the compound of formula ABC3 in the presence of trichloracetonitrile to the compound of formula ABC4

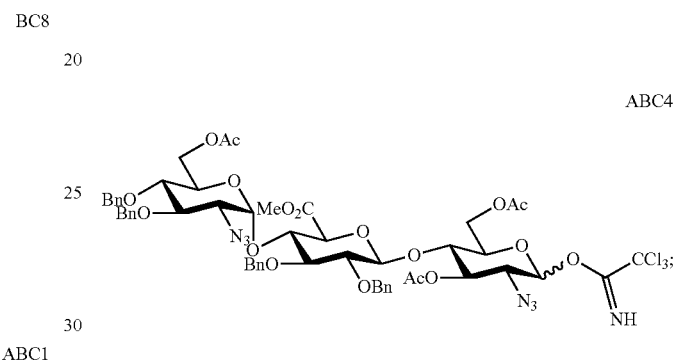

ABC4 v) converting the compound of formula ABC4 in the presence of a promoter and a thiol to provide the compound of formula ABC5;

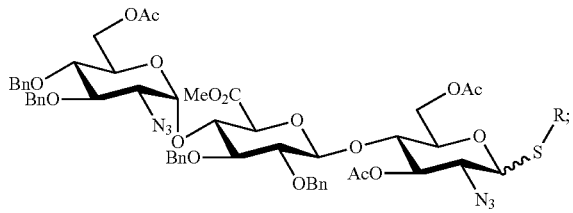

ABC5 vi) contacting the compound of formula ABC5 with the compound of formula DE4 in the presence of a promoter, and/or a radical initiator

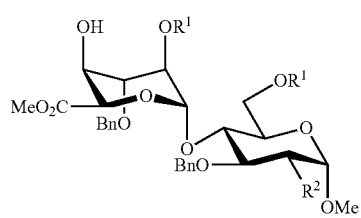

DE4 to obtain the compound of formula ABCDE1
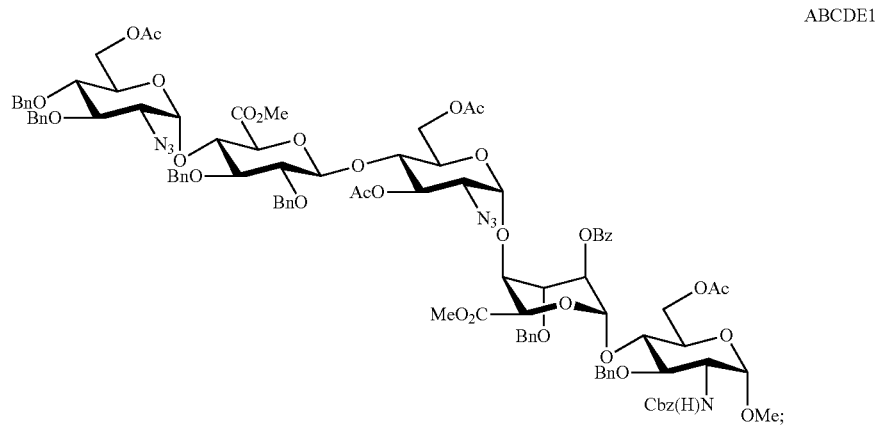
ABCDE1
vii) converting the compound of formula ABCDE1 in the presence of a peroxide and a base to the compound of formula ABCDE2
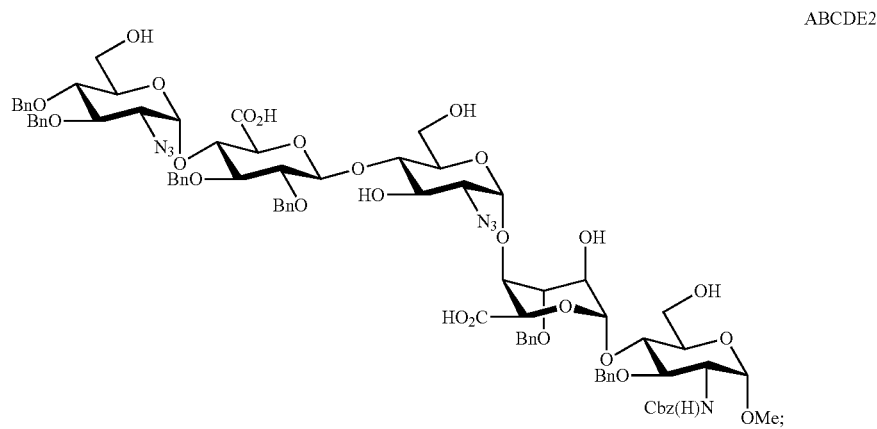
ABCDE2
viii) converting the compound of formula ABCDE2 in the presence of a sulfating agent to the compound of formula ABCDE3
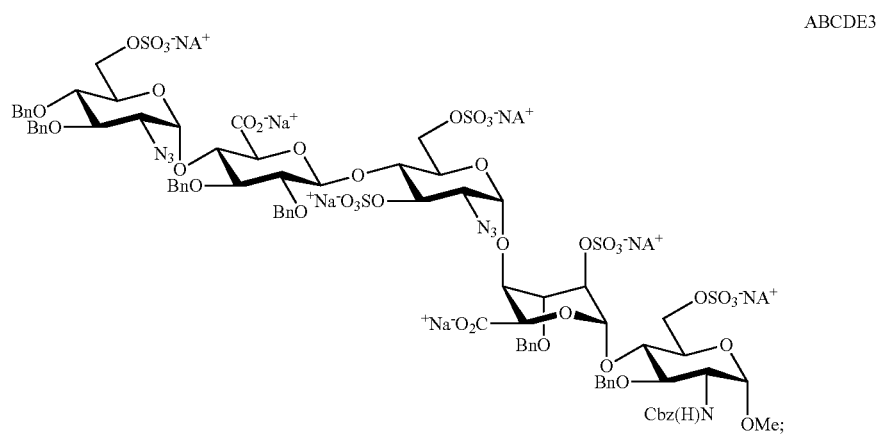
ABCDE3 ix) converting the compound of formula ABCDE3 in the presence of a hydrogenating catalyst and $H_2$ to the compound of formula ABCDE4

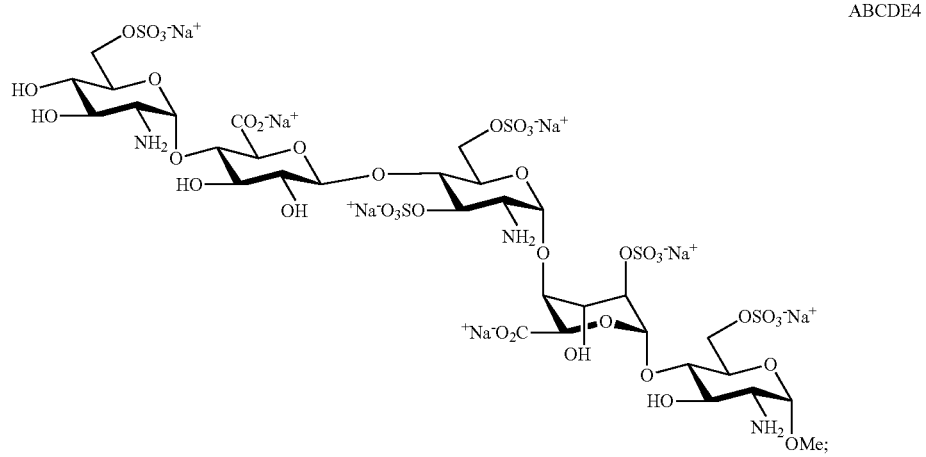

ABCDE4 x) converting the compound of formula ABCDE4 to Fondaparinux sodium of formula ABCDE5 using a sulfonating reagent

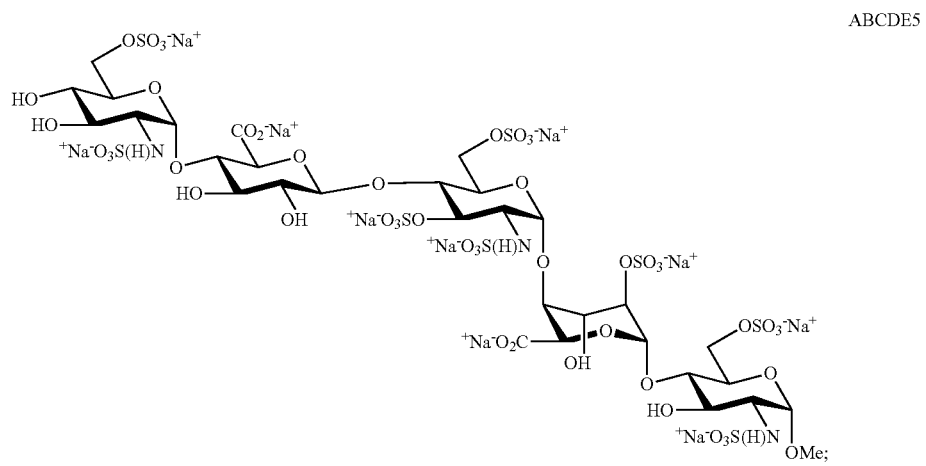

ABCDE5 wherein
R is selected from the group consisting of alkyl, phenyl, benzyl, substituted alkyl, substituted phenyl, substituted benzyl; and
$R^1$ is acetyl or benzoyl; and
$R^2$ is azide or NHCbz.

4. A process of claim 1, wherein step i) further comprises a) converting a compound of formula A4:

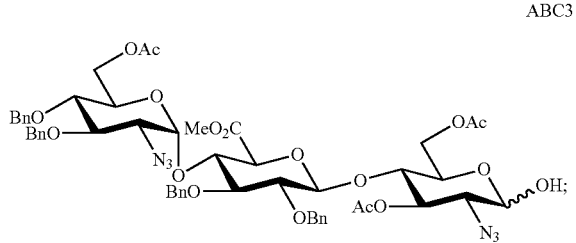

to a compound of formula A5:

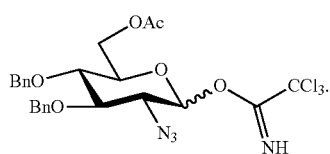

5. A process of claim 4, wherein step a) is conducted in the presence of a base and trichloroacetonitrile.

6. A process of claim 5, wherein the base is selected from the group consisting of DBU and potassium carbonate.

7. A process of claim 1, wherein step i) is conducted in the presence of promoter.

8. A process of claim 3 or 7, wherein the promoter is selected from the group consisting of triethylsilyl trifluoromethanesulfonate (TESOTf), trimethylsilyltrifluoromethanesulfonate (TMSOTf), tert-butyldimethylsilyl trifluoromethanesulfonate (TBSOTf), and mixtures thereof.

9. A process of claim 3, wherein the radical initiator is selected from the group consisting of N-iodosuccinimide, and N-bromosuccinimide.

10. A process of claim 3, wherein ABC5 is ABC5a:

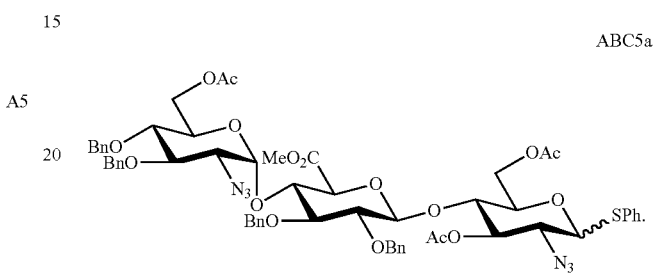

* * * * *